| United States Patent [19] | [11] Patent Number: 4,950,831 |
| --- | --- |
| Staton et al. | [45] Date of Patent: Aug. 21, 1990 |

[54] COUPLING PROCESS

[75] Inventors: James S. Staton; Ronald A. Turnblad, Jr.; Robert B. Agee, all of Orangeburg, S.C.

[73] Assignee: Ethyl Corporation, Richmond, Va.

[21] Appl. No.: 413,961

[22] Filed: Sep. 28, 1989

[51] Int. Cl.$^5$ .............................................. C07C 2/64
[52] U.S. Cl. .................................... 585/447; 585/452; 585/453
[58] Field of Search ..................... 585/452, 453, 447

[56] References Cited

U.S. PATENT DOCUMENTS

| | | | |
| --- | --- | --- | --- |
| 3,006,976 | 10/1961 | Shaw et al. | 585/453 |
| 3,449,455 | 6/1969 | Napolitano et al. | 585/453 |
| 3,470,265 | 9/1969 | Sprow | 585/447 |
| 4,179,580 | 12/1979 | Cobb . | |
| 4,356,337 | 10/1982 | Pez et al. | 585/350 |

FOREIGN PATENT DOCUMENTS

| | | | |
| --- | --- | --- | --- |
| 0734128 | 7/1955 | United Kingdom | 585/452 |
| 0857894 | 1/1961 | United Kingdom | 585/452 |

*Primary Examiner*—Asok Pal
*Assistant Examiner*—J. Saba
*Attorney, Agent, or Firm*—Patricia J. Hogan; Richard J. Hammond

[57] ABSTRACT

An alkene is coupled with an aromatic hydrocarbon having an active hydrogen on a saturated alpha-carbon in the presence of an unsupported alkali metal as a catalyst under high shear agitation conditions. In preferred embodiments of the invention, the alkene is an alkene of 2-20 carbons, such as ethene or propene; the active hydrogen-containing aromatic hydrocarbon is an alkylbenzene, such as toluene; the alkali metal is potassium or a potassium alloy; and the high shear agitation conditions are attained by operating a turbine-type impeller at a tip speed of at least about 5 m/sec.

16 Claims, No Drawings

COUPLING PROCESS

FIELD OF INVENTION

This invention relates to a process for coupling an alkene with an aromatic hydrocarbon having an active hydrogen on a saturated alpha-carbon.

BACKGROUND

As disclosed, e.g., in U.S. Pat. No. 4,179,580 (Cobb), it is known that supported and unsupported alkali metals are useful as catalysts in the coupling of ethylenically-unsaturated hydrocarbons with aromatic hydrocarbons having an active hydrogen on a saturated alpha-carbon. The supported alkali metals are more effective than the corresponding unsupported alkali metals in such reactions, but the use of a support has the drawbacks of involving filtration, handling, treatment, and disposal costs which it would be desirable to avoid.

SUMMARY OF INVENTION

An object of this invention is to provide a novel process for coupling an alkene with an aromatic hydrocarbon having an active hydrogen on a saturated alpha-carbon.

Another object is to provide such a process which utilizes an unsupported alkali metal as a catalyst.

A further object is to provide such a process in which the reaction rate is increased.

These and other objects are attained by coupling an alkene with an aromatic hydrocarbon having an active hydrogen on a saturated alpha-carbon in the presence of an unsupported alkali metal as a catalyst while subjecting the reaction mixture to high shear agitation conditions throughout the reaction.

DETAILED DESCRIPTION

The alkene which is coupled with the aromatic hydrocarbon in the practice of the invention may be any of the alkenes that are known to be useful in such reactions, such as ethene, propene, 1-butene, 2-butene, isobutene, 1-pentene, 2-pentene, 3-methyl-1-butene, 2-methyl-2-butene, 1-hexene, 2-hexene, 3-hexene, 4-methyl-1-pentene, 3-methyl-1-pentene, 4-methyl-2-pentene, 1-heptene, 2-heptene, 2-octene, 4-nonene, 1-decene, 2-decene, 1-dodecene, 3-tetradecene, 5-hexadecene, 6-methyl-4-heptadecene, 1-eicosene, etc. However, it is generally an alkene corresponding to the formula $QQ'C=CTT'$, in which Q, Q', T, and T' are independently selected from hydrogen and alkyl groups of up to 20 carbons; and it is apt preferably to be an alkene of up to 20 carbons. Particularly preferred alkenes are ethene and propene.

The aromatic hydrocarbon having an active hydrogen on a saturated alpha-carbon may be any such compound that is known to be useful in such reactions, such as toluene, ethylbenzene, n-propylbenzene, isopropylbenzene, n-butylbenzene, sec-butylbenzene, isobutylbenzene, n-eicosylbenzene, o-, m-, and p-xylenes, o-, m-, and p-ethyltoluenes, 1,3,5-trimethylbenzene, 1,2,4,5- and 1,2,3,5-tetramethylbenzenes, p-diisopropylbenzene, 1- and 2-methylnaphthalenes, dimethylnaphthalenes, 1-ethyl-4-n-octadecylnaphthalene, 1,4-di-n-pentylnaphthalene, 1,2,3,4-tetrahydronaphthalene, indan, cyclohexylbenzene, methylcyclohexylbenzene, diphenylmethane, etc. However, it is generally a hydrocarbon corresponding to the formula $RR'R''CH$, in which R is an aryl group of up to 20 carbons and R' and R" are independently selected from hydrogen and alkyl and aryl groups of up to 20 carbons; and it is apt preferably to be an alkylbenzene having one or more ar-alkyl groups. A particularly preferred aromatic hydrocarbon is toluene.

The mol ratio of alkene to aromatic hydrocarbon varies with the particular reactants employed and the products desired, particularly since the aromatic hydrocarbon may have one or more active hydrogens, and it may be desired to react the alkene with only one or with more than one active hydrogen in the aromatic hydrocarbon. It is frequently preferred to employ the reactants in the stoichiometric amounts appropriate for the preparation of the desired product. However, either reactant can be used in excess.

As in Cobb, the teachings of which are incorporated herein in toto by reference, the alkali metal employed as a catalyst may be lithium, sodium, potassium, rubidium, or cesium; and it appropriately has its surface area increased by being finely divided or liquid. However, it is preferably potassium or a potassium alloy, e.g., a sodium-potassium alloy having a potassium content of 40-90% by weight. The amount of alkali metal used is a catalytic amount, generally about 2-10 mole %, based on the amount of either of the reactants when they are employed in equimolar amounts or on the amount of the major reactant when they are not utilized in equimolar amounts.

The reaction is conducted by heating a mixture of the alkene, the active hydrogen-containing aromatic hydrocarbon, and the catalyst, under substantially anhydrous conditions at a suitable temperature, generally about 100°-300° C., preferably about 175°-200° C., and under high shear agitation conditions to couple the reactants. It is generally conducted in the absence of a diluent or in the presence of an excess of the active hydrogen-containing aromatic hydrocarbon as the sole diluent. However, an inert diluent can be used if desired. Exemplary of such diluents are liquid alkanes, cycloalkanes, and aromatic hydrocarbons, such as pentane, hexane, isooctane, cyclohexane, naphthalene, decahydronaphthalene, white oils, etc.

The high shear agitation conditions are maintained throughout the reaction and are preferably attained by operating a turbine-type impeller at a tip speed of at least about 5 m/sec., more preferably at least about 5.5 m/sec., most preferably about 5.5-9.0 m/sec. However, different types of agitators may be used to produce equivalent high shear agitation conditions if desired.

The process of the invention proceeds at a faster rate than comparable processes conducted under conventional agitation conditions, facilitates recycle of the catalyst because of not requiring dispersing agents such as those used in most dispersion reactions, and is particularly advantageous as a means of alkylating alkylaromatic compounds, especially alkylbenzenes, to form compounds useful as solvents, internal standards, intermediates for polymers, pharmaceuticals, or pesticides, etc.

The following examples are given to illustrate the invention and are not intended as a limitation thereof.

EXAMPLE I

A 1-L Parr autoclave provided with a high shear turbine-type impeller was charged with 4.3g of NaK (an alloy having a K content of 78% by weight) and 428g of toluene. The mixture was heated to 160° C. under normal agitation, i.e., an agitator tip speed of 1.5 m/sec.; and the agitator tip speed was then increased to 5.7 m/sec. The mixture was agitated at this speed for 15 minutes, after which the temperature was increased to 190° C. Then 160 g of propene was fed over a period of 30 minutes while the temperature was maintained below 200° C. with cooling and the pressure below 2.8 MPa by regulating the propene feed rate. The autoclave was kept at 190° C. for one hour, and agitation was then slowed to normal. The NaK was deactivated by the addition of 12 g of isopropanol and 142 g of water. Analysis of the organic phase by gas chromatography showed that the reaction resulted in conversion to isobutylbenzene at the rate of 0.975 mol/hr. This compares with a conversion rate of only about 0.75 mol/hr. when diatomaceous earth- or potassium carbonate-supported NaK is employed as the catalyst and normal agitation conditions are maintained throughout the reaction.

EXAMPLE II

Example I was repeated except that the agitator tip speed was increased to 7.1 m/sec. instead of 5.7 m/sec. The reaction resulted in conversion to isobutylbenzene at a rate of 1.057 mols/hr.

The preceding examples show that the practice of the invention makes it possible to achieve reaction rates even faster than those achieved with a supported alkali metal catalyst under normal agitation conditions, thus permitting the elimination of the support and its consequent disadvantages. The following examples demonstrate that these higher reaction rates are not achieved with unsupported catalysts when agitator tip speeds of less than 5 m/sec. are employed or agitator tip speeds of at least 5 m/sec are not maintained throughout the reaction.

COMPARATIVE EXAMPLE A

Example I was repeated except that the agitator tip speed was increased to only 1.9 m/sec. instead of 5.7 m/sec. The reaction resulted in conversion to isobutylbenzene at a rate of only 0.0389 mole/hr.

COMPARATIVE EXAMPLE B

Example I was repeated except that the agitator tip speed was increased to only 2.8 m/sec. instead of 5.7 m/sec. The reaction resulted in conversion to isobutylbenzene at a rate of only 0.1458 mole/hr.

COMPARATIVE EXAMPLE C

Example I was repeated except that the agitator tip speed was increased to only 4.0 m/sec. instead of 5.7 m/sec. The reaction resulted in conversion to isobutylbenzene at a rate of only 0.493 mole/hr.

COMPARATIVE EXAMPLE D

Example I was essentially repeated except that the NaK/toluene mixture was heated to 120° C. and agitated at a tip speed of 5.7 m/sec, after which the resulting dispersion was transferred to a second 1-L Parr in which normal agitation was employed during the heating to 190° C. and throughout the reaction. The reaction resulted in conversion to isobutylbenzene at a rate of only 0.0002 mole/hr.

It is obvious that many variations may be made in the products and processes set forth above without departing from the spirit and scope of this invention.

What is claimed is:

1. In a process for coupling an alkene with an aromatic hydrocarbon having an active hydrogen on a saturated alpha-carbon in the presence of an unsupported alkali metal as a catalyst, the improvement which comprises subjecting the reaction mixture to high shear agitation with an agitator having a tip speed of at least about 5 m/sec.

2. The process of claim 1 wherein the alkene is a compound corresponding to the formula $QQ'C=CTT'$, in which Q, Q', T, and T' are independently selected from hydrogen and alkyl groups of up to 20 carbons.

3. The process of claim 2 wherein the alkene contains 2-20 carbons.

4. The process of claim 3 wherein the alkene is propene.

5. The process of claim 1 wherein the aromatic hydrocarbon is a hydrocarbon corresponding to the formula $RR'R''CH$, in which R is an aryl group of up to 20 carbons and R' and R'' are independently selected from hydrogen and alkyl and aryl groups of up to 20 carbons.

6. The process of claim 5 wherein the aromatic hydrocarbon is an alkylbenzene.

7. The process of claim 6 wherein the alkylbenzene is toluene.

8. The process of claim 1 wherein the alkali metal is potassium or a potassium alloy.

9. The process of claim 8 wherein the alkali metal is potassium.

10. The process of claim 8 wherein the alkali metal is NaK.

11. The process of claim 1 wherein the high shear agitation conditions are attained by operating a turbine-type impeller.

12. The process of claim 11 wherein the tip speed is at least about 5.5 m/sec.

13. The process of claim 12 wherein the tip speed is about 5.5-9.0 m/sec.

14. The process of claim 1 which is conducted at a temperature of about 100°-300° C.

15. The process of claim 14 wherein the reaction temperature is about 175°-200° C.

16. The process of claim 1 wherein propene is coupled with toluene at about 175°-200° C. in the presence of an unsupported NaK catalyst under high shear agitation conditions attained by operating a turbine-type impeller at a tip speed of about 5.5-9.0 m/sec.

* * * * *